US012797322B2

(12) United States Patent
Punyani et al.

(10) Patent No.: US 12,797,322 B2
(45) Date of Patent: *Nov. 17, 2026

(54) REDUCTION OF OIL TRANSFER FROM SCALP TO HAIR WITH INCREASING POLARITY OF HAIR

(71) Applicant: The Procter & Gamble Company, Cincinnati, OH (US)

(72) Inventors: Supriya Punyani, Singapore (SG); Husen Kartasasmita Kang, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 172 days.

This patent is subject to a terminal disclaimer.

(21) Appl. No.: 18/469,588

(22) Filed: Sep. 19, 2023

(65) Prior Publication Data

US 2024/0108567 A1 Apr. 4, 2024

Related U.S. Application Data

(60) Provisional application No. 63/409,077, filed on Sep. 22, 2022.

(51) Int. Cl.
*A61K 8/72* (2006.01)
*A61Q 5/00* (2006.01)
*A61Q 5/12* (2006.01)

(52) U.S. Cl.
CPC ................ *A61K 8/72* (2013.01); *A61Q 5/008* (2013.01); *A61Q 5/12* (2013.01); *A61K 2800/5426* (2013.01)

(58) Field of Classification Search
CPC .. A61K 8/72; A61K 2800/5426; A61Q 5/008; A61Q 5/12
See application file for complete search history.

(56) References Cited

U.S. PATENT DOCUMENTS

| | | | |
|---|---|---|---|
| 2,879,231 | A | 3/1959 | Marshall |
| 3,709,437 | A | 1/1973 | Wright |
| 3,950,532 | A | 4/1976 | Bouillon et al. |
| 3,959,160 | A | 5/1976 | Horsler et al. |
| 4,309,119 | A | 1/1982 | Wittersheim |
| 4,329,334 | A | 5/1982 | Su et al. |
| 4,454,060 | A | 6/1984 | Lai et al. |
| 4,554,098 | A | 11/1985 | Klisch et al. |
| 4,686,254 | A | 8/1987 | Lochhead et al. |
| 4,726,945 | A | 2/1988 | Patel |
| 4,800,197 | A | 1/1989 | Kowcz |
| 4,839,166 | A | 6/1989 | Grollier et al. |
| 4,867,971 | A | 9/1989 | Ryan et al. |
| 4,885,107 | A | 12/1989 | Wetzel |
| 4,997,641 | A | 3/1991 | Hartnett |
| 5,221,530 | A | 6/1993 | Janchitraponvej et al. |
| 5,233,087 | A | 8/1993 | Cripe |
| 5,294,644 | A | 3/1994 | Login et al. |
| 5,332,569 | A | 7/1994 | Wood et al. |
| 5,364,031 | A | 11/1994 | Taniguchi et al. |
| 5,374,421 | A | 12/1994 | Tashiro |
| 5,409,695 | A | 4/1995 | Abrutyn et al. |
| 5,415,810 | A | 5/1995 | Lee et al. |
| 5,417,965 | A | 5/1995 | Janchitraponvej et al. |
| 5,439,682 | A | 8/1995 | Wivell |
| 5,441,659 | A | 8/1995 | Minor |
| 5,500,217 | A | 3/1996 | Austin et al. |
| 5,560,918 | A | 10/1996 | Wivell |
| 5,578,298 | A | 11/1996 | Berthiaume |
| 5,599,549 | A | 2/1997 | Wivell |
| 5,624,666 | A | 4/1997 | Coffindaffer et al. |
| 5,635,469 | A | 6/1997 | Fowler et al. |
| 5,675,013 | A | 10/1997 | Hani et al. |
| 5,716,626 | A | 2/1998 | Sakurai et al. |
| 5,747,436 | A | 5/1998 | Patel |
| 5,776,444 | A | 7/1998 | Birtwistle et al. |
| 5,816,446 | A | 10/1998 | Steindorf et al. |
| 5,830,440 | A | 11/1998 | Sturla et al. |
| 5,853,618 | A | 12/1998 | Barker |
| 5,856,293 | A | 1/1999 | Gambogi et al. |
| 5,902,225 | A | 5/1999 | Monson |
| 5,922,662 | A | 7/1999 | Thomas |
| 5,925,603 | A | 7/1999 | D, Angelo |

(Continued)

FOREIGN PATENT DOCUMENTS

| | | | |
|---|---|---|---|
| CA | 2078375 | A1 | 3/1994 |
| CN | 1286612 | A | 3/2001 |

(Continued)

OTHER PUBLICATIONS

PCT Search Report and Written Opinion for PCT/US2023/074518 dated Jan. 22, 2024; 15 Pages.
"Anti-Dandruff Shampoo", Mintel Database, Record No. 752198, dated Aug. 2007 ; pp. 1-3.
"Belsil DM-500000", Wacker, URL: https://www.wacker.com/h/en-us/silicone-fluids-emulsions/silicone-fluids-inci/belsil-dm-500000/p/000009670, Jul. 1, 2020, 3 pages.
"Dandruff Control Shampoo", Mintel Database, Record No. 2300131, dated Jan. 2014; pp. 1-2.
"Natural Detangling Shampoo", Mintel Database, dated Sep. 13, 2017; 2 pages.
"Optimizing Surfactant Systems Thickened with Carbopol®* ETD 2020 Polymer Using a Statistical Design", Technical Data Sheet, Lubrizol, Oct. 15, 2007, 5 pages.

(Continued)

*Primary Examiner* — Jianfeng Song
(74) *Attorney, Agent, or Firm* — Linda M. Sivik

(57) ABSTRACT

A hair care composition that includes 0.05% to 5% of a hydrophilic polymer selected from the group consisting of polyvinylalcohols, polyacrylates ethers, polyvinyl pyrrolidones, polyvinyl pyrrolidones copolymer, vinyl cyanides, vinyl phosphates, vinyl phosphonates, vinyl sulfates, vinyl sulfonates, polyamines, cellulose, collagen, polyethylene glycols, polycarboxylate co-polymers of maleic/olefin, and mixtures thereof. The hair care composition provides a water contact angle of <85 to hair reduces oil transfer to hair.

16 Claims, No Drawings

(56) References Cited

U.S. PATENT DOCUMENTS

| | | | |
|---|---|---|---|
| 5,944,229 | A | 8/1999 | Rokkjaer |
| 5,980,877 | A | 11/1999 | Baravetto |
| 5,985,939 | A | 11/1999 | Minor |
| 6,015,547 | A | 1/2000 | Yam |
| 6,015,780 | A | 1/2000 | Llosas Bigorra et al. |
| 6,020,303 | A | 2/2000 | Cripe et al. |
| 6,039,933 | A | 3/2000 | Samain et al. |
| 6,046,152 | A | 4/2000 | Vinson et al. |
| 6,060,443 | A | 5/2000 | Cripe et al. |
| 6,087,309 | A | 7/2000 | Vinson et al. |
| 6,087,320 | A | 7/2000 | Urfer et al. |
| 6,110,451 | A | 8/2000 | Matz et al. |
| 6,133,222 | A | 10/2000 | Vinson et al. |
| 6,147,038 | A | 11/2000 | Halloran |
| 6,153,569 | A | 11/2000 | Halloran |
| 6,162,834 | A | 12/2000 | Sebillotte-Arnaud et al. |
| 6,231,844 | B1 | 5/2001 | Nambu |
| 6,268,431 | B1 | 7/2001 | Snyder et al. |
| 6,284,225 | B1 | 9/2001 | Bhatt |
| 6,329,331 | B1 | 12/2001 | Aronson |
| 6,335,312 | B1 | 1/2002 | Coffindaffer et al. |
| 6,423,305 | B1 | 7/2002 | Cauwet-Martin et al. |
| 6,451,300 | B1 | 9/2002 | Dunlop et al. |
| 6,511,669 | B1 | 1/2003 | Garnier et al. |
| 6,565,863 | B1 | 5/2003 | Guillou et al. |
| 6,579,907 | B1 | 6/2003 | Sebillotte-Arnaud et al. |
| 6,627,585 | B1 | 9/2003 | Steer |
| 6,642,194 | B2 | 11/2003 | Harrison |
| 6,649,155 | B1 | 11/2003 | Dunlop et al. |
| 6,716,455 | B2 | 4/2004 | Birkel |
| 6,743,760 | B1 | 6/2004 | Hardy et al. |
| 6,827,795 | B1 | 12/2004 | Kasturi et al. |
| 6,897,253 | B2 | 5/2005 | Schmucker-castner |
| 6,930,078 | B2 | 8/2005 | Wells |
| 6,992,054 | B2 | 1/2006 | Lee et al. |
| 7,217,752 | B2 | 5/2007 | Schmucker-Castner et al. |
| 7,220,408 | B2 | 5/2007 | Decoster et al. |
| 7,223,385 | B2 | 5/2007 | Gawtrey et al. |
| 7,485,289 | B2 | 2/2009 | Gawtrey et al. |
| 7,504,094 | B2 | 3/2009 | Decoster et al. |
| 7,531,497 | B2 | 5/2009 | Midha et al. |
| 7,541,320 | B2 | 6/2009 | Dabkowski et al. |
| 7,659,233 | B2 | 2/2010 | Hurley et al. |
| 7,666,825 | B2 | 2/2010 | Wagner et al. |
| 7,807,766 | B2 | 10/2010 | Albers |
| 7,820,609 | B2 | 10/2010 | Soffin et al. |
| 7,829,514 | B2 | 11/2010 | Paul et al. |
| 7,928,053 | B2 | 4/2011 | Hecht et al. |
| 7,977,288 | B2 | 7/2011 | SenGupta |
| 8,084,407 | B2 | 12/2011 | Soffin et al. |
| 8,088,721 | B2 | 1/2012 | Soffin et al. |
| 8,119,168 | B2 | 2/2012 | Johnson |
| 8,124,063 | B2 | 2/2012 | Harichian et al. |
| 8,300,949 | B2 | 10/2012 | Xu |
| 8,343,469 | B2 | 1/2013 | Bierganns et al. |
| 8,388,690 | B2 | 3/2013 | Singhatat et al. |
| 8,388,699 | B2 | 3/2013 | Wood |
| 8,401,304 | B2 | 3/2013 | Sportvision |
| 8,435,501 | B2 | 5/2013 | Peffly et al. |
| 8,437,556 | B1 | 5/2013 | Saisan |
| 8,491,877 | B2 | 7/2013 | Schwartz et al. |
| 8,580,725 | B2 | 11/2013 | Kuhlman et al. |
| 8,609,600 | B2 | 12/2013 | Warr et al. |
| 8,628,760 | B2 | 1/2014 | Carter et al. |
| 8,629,095 | B2 | 1/2014 | Deleersnyder |
| 8,653,014 | B2 | 2/2014 | Hilvert |
| 8,675,919 | B2 | 3/2014 | Maladen |
| 8,680,035 | B2 | 3/2014 | Kuhlman et al. |
| 8,699,751 | B2 | 4/2014 | Maladen |
| 8,709,385 | B2 | 4/2014 | Tamarkin |
| 8,741,363 | B2 | 6/2014 | Albrecht et al. |
| 8,771,765 | B1 | 7/2014 | Fernandez |
| 8,795,635 | B2 | 8/2014 | Tamarkin et al. |
| 8,883,698 | B2 | 11/2014 | Scheibel et al. |
| 9,006,162 | B1 | 4/2015 | Rizk |
| 9,034,792 | B2 | 5/2015 | Stark et al. |
| 9,102,907 | B2 | 8/2015 | Hloucha |
| 9,126,163 | B2 | 9/2015 | Giessler-blank et al. |
| 9,186,642 | B2 | 11/2015 | Dihora et al. |
| 9,265,727 | B1 | 2/2016 | Lowenborg |
| 9,296,550 | B2 | 3/2016 | Smith |
| 9,308,398 | B2 | 4/2016 | Hutton et al. |
| 9,428,616 | B2 | 8/2016 | Wagner |
| 9,512,275 | B2 | 12/2016 | Wagner |
| 9,610,239 | B2 | 4/2017 | Feng |
| 9,656,104 | B2 | 5/2017 | Hloucha |
| 9,682,021 | B2 | 6/2017 | Tamarkin et al. |
| 9,776,787 | B2 | 10/2017 | Nakajima |
| 9,949,901 | B2 | 4/2018 | Zhao et al. |
| 9,968,535 | B2 | 5/2018 | Kitko |
| 9,968,537 | B2 | 5/2018 | Sharma |
| 9,993,419 | B2 | 6/2018 | Glenn, Jr. |
| 9,993,420 | B2 | 6/2018 | Glenn, Jr. et al. |
| 10,227,551 | B2 | 3/2019 | Arhancet et al. |
| 10,311,575 | B2 | 6/2019 | Stofel |
| 10,322,072 | B2 | 6/2019 | Glenn, Jr. et al. |
| 10,406,094 | B2 | 9/2019 | Punyani et al. |
| 10,426,713 | B2 | 10/2019 | Song |
| 10,441,519 | B2 | 10/2019 | Zhao |
| 10,561,591 | B2 | 2/2020 | Punyani |
| 10,653,590 | B2 | 5/2020 | Torres Rivera |
| 10,653,609 | B2 | 5/2020 | Kroger Lyons |
| 10,799,434 | B2 | 10/2020 | Torres Rivera |
| 10,842,720 | B2 | 11/2020 | Thompson |
| 10,881,597 | B2 | 1/2021 | Lane et al. |
| 10,888,505 | B2 | 1/2021 | Johnson |
| 10,912,732 | B2 | 2/2021 | Gillis |
| 11,116,704 | B2 | 9/2021 | Song et al. |
| 11,179,309 | B2 | 11/2021 | Chang et al. |
| 11,433,070 | B2 | 9/2022 | Richards et al. |
| 11,523,979 | B2 | 12/2022 | Chang et al. |
| 11,684,558 | B2 | 6/2023 | Chang et al. |
| 11,980,612 | B2 | 5/2024 | Richards |
| 2001/0000467 | A1 | 4/2001 | Murray |
| 2001/0006088 | A1 | 7/2001 | Lyle |
| 2001/0006621 | A1 | 7/2001 | Coupe et al. |
| 2001/0016565 | A1 | 8/2001 | Bodet et al. |
| 2002/0028182 | A1 | 3/2002 | Dawson |
| 2002/0037299 | A1 | 3/2002 | Turowski-Wanke et al. |
| 2002/0172648 | A1 | 11/2002 | Hehner et al. |
| 2002/0193265 | A1 | 12/2002 | Perron et al. |
| 2002/0197213 | A1 | 12/2002 | Schmenger et al. |
| 2003/0022799 | A1 | 1/2003 | Alvarado et al. |
| 2003/0049292 | A1 | 3/2003 | Turowski-Wanke et al. |
| 2003/0050150 | A1 | 3/2003 | Tanaka |
| 2003/0059377 | A1 | 3/2003 | Riley |
| 2003/0069148 | A1 | 4/2003 | Booker |
| 2003/0083210 | A1 | 5/2003 | Goldberg |
| 2003/0108501 | A1 | 6/2003 | Hofrichter |
| 2003/0147842 | A1 | 8/2003 | Restle et al. |
| 2003/0154561 | A1 | 8/2003 | Patel |
| 2003/0161802 | A1 | 8/2003 | Flammer |
| 2003/0180246 | A1 | 9/2003 | Frantz et al. |
| 2003/0185867 | A1 | 10/2003 | Kerschner et al. |
| 2003/0223951 | A1 | 12/2003 | Geary et al. |
| 2003/0228272 | A1 | 12/2003 | Amjad et al. |
| 2004/0014879 | A1 | 1/2004 | Denzer et al. |
| 2004/0101504 | A1 | 5/2004 | Kinscherf et al. |
| 2004/0144863 | A1 | 7/2004 | Kendrick |
| 2004/0229963 | A1 | 11/2004 | Stephane |
| 2004/0234484 | A1 | 11/2004 | Peffly |
| 2004/0235689 | A1 | 11/2004 | Sakai et al. |
| 2005/0019293 | A1 | 1/2005 | Suriano et al. |
| 2005/0020468 | A1 | 1/2005 | Frantz et al. |
| 2005/0048021 | A1 | 3/2005 | Salem |
| 2005/0136011 | A1 | 6/2005 | Nekludoff |
| 2005/0152863 | A1 | 7/2005 | Brautigam |
| 2005/0201967 | A1 | 9/2005 | Albrecht et al. |
| 2005/0202984 | A1 | 9/2005 | Schwartz et al. |
| 2005/0233929 | A1 | 10/2005 | Queen |
| 2006/0002880 | A1 | 1/2006 | Peffly |
| 2006/0030509 | A1 | 2/2006 | Modi |
| 2006/0034778 | A1 | 2/2006 | Kitano et al. |
| 2006/0035807 | A1 | 2/2006 | Kasturi |

(56) References Cited

U.S. PATENT DOCUMENTS

2006/0057075 A1 3/2006 Arkin et al.
2006/0057097 A1 3/2006 Derici
2006/0079417 A1 4/2006 Wagner
2006/0079418 A1 4/2006 Wagner et al.
2006/0079419 A1 4/2006 Wagner et al.
2006/0079420 A1 4/2006 Wagner et al.
2006/0079421 A1 4/2006 Wagner et al.
2006/0090777 A1 5/2006 Hecht et al.
2006/0110415 A1 5/2006 Gupta
2006/0120982 A1 6/2006 Derici et al.
2006/0120988 A1 6/2006 Bailey et al.
2006/0135397 A1 6/2006 Bissey-beugras
2006/0171911 A1 8/2006 Schwartz et al.
2006/0183662 A1 8/2006 Crotty
2006/0210139 A1 9/2006 Carroll
2006/0229227 A1 10/2006 Goldman
2006/0252662 A1 11/2006 Soffin
2006/0276357 A1 12/2006 Smith, III et al.
2006/0292104 A1 12/2006 Guskey
2007/0027051 A1 2/2007 Staudigel et al.
2007/0072781 A1 3/2007 Soffin et al.
2007/0092547 A1 4/2007 Birnbaum
2007/0110700 A1 5/2007 Wells
2007/0154402 A1 7/2007 Trumbore et al.
2007/0155637 A1 7/2007 Smith, III et al.
2007/0160555 A1 7/2007 Staudigel et al.
2007/0179207 A1 8/2007 Fernandez de Castro et al.
2007/0225193 A1 9/2007 Kuhlman et al.
2007/0244027 A1 10/2007 Sivik et al.
2007/0259794 A1 11/2007 Wachsberg
2007/0269397 A1 11/2007 Terada
2007/0292380 A1 12/2007 Staudigel
2008/0008668 A1 1/2008 Harichian et al.
2008/0019928 A1 1/2008 Franzke
2008/0063618 A1 3/2008 Johnson
2008/0096786 A1 4/2008 Holt et al.
2008/0138442 A1 6/2008 Johnson
2008/0152610 A1 6/2008 Cajan
2008/0160093 A1 7/2008 Schwartz et al.
2008/0206179 A1 8/2008 Peffly et al.
2008/0220103 A1 9/2008 Birnbaum et al.
2008/0260655 A1 10/2008 Tamarkin et al.
2008/0260665 A1 10/2008 Guerchet et al.
2008/0261844 A1 10/2008 Ruppert et al.
2008/0317698 A1 12/2008 Wells et al.
2009/0029900 A1 1/2009 Cetti et al.
2009/0041702 A1 2/2009 Molenda
2009/0062406 A1 3/2009 Loeffler
2009/0155383 A1 6/2009 Kitko et al.
2009/0178210 A1 7/2009 Bistram
2009/0197784 A1 8/2009 Ainger
2009/0221463 A1 9/2009 Kitko et al.
2009/0222956 A1 9/2009 Cush et al.
2009/0246236 A1 10/2009 Kitko
2009/0312224 A1 12/2009 Yang et al.
2009/0324505 A1 12/2009 Seidling
2010/0183539 A1 7/2010 Bernhardt
2010/0215775 A1 8/2010 Schmaus et al.
2010/0234366 A1 9/2010 Van et al.
2010/0310644 A1 12/2010 Liebmann
2011/0008267 A1 1/2011 Arkin et al.
2011/0055978 A1 3/2011 Jamet et al.
2011/0123582 A1 5/2011 Smets et al.
2011/0165107 A1 7/2011 Derks et al.
2011/0171155 A1 7/2011 Federle
2011/0190129 A1 8/2011 Bell et al.
2011/0195846 A1 8/2011 Troppmann et al.
2011/0217340 A1 9/2011 Angus et al.
2011/0232668 A1 9/2011 Hoffmann et al.
2011/0245126 A1 10/2011 Tsaur et al.
2011/0268778 A1 11/2011 Dihora
2011/0269657 A1 11/2011 Dihora et al.
2011/0305739 A1 12/2011 Royce
2011/0319790 A1 12/2011 Kost et al.
2012/0014901 A1 1/2012 Sunkel et al.
2012/0022021 A1 1/2012 Rademacher et al.
2012/0027699 A1 2/2012 Rosa et al.
2012/0031419 A1 2/2012 Batt
2012/0034173 A1 2/2012 Batt
2012/0087883 A1 4/2012 Leray et al.
2012/0100091 A1 4/2012 Hata et al.
2012/0100092 A1 4/2012 Murray
2012/0291911 A1 11/2012 Smith
2012/0309660 A1 12/2012 Kawasoe
2012/0316095 A1 12/2012 Wei et al.
2013/0034515 A1 2/2013 Stone et al.
2013/0045285 A1 2/2013 Stella et al.
2013/0053295 A1 2/2013 Kinoshita et al.
2013/0053300 A1 2/2013 Scheibel et al.
2013/0089586 A1 4/2013 Johnson et al.
2013/0089587 A1 4/2013 Staudigel
2013/0115173 A1 5/2013 Trumbore et al.
2013/0143784 A1 6/2013 Rizk
2013/0150338 A1 6/2013 Ananthapadmanabhan
2013/0156712 A1 6/2013 Frantz
2013/0189212 A1 7/2013 Jawale et al.
2013/0196852 A1 8/2013 Rannard et al.
2013/0197275 A1 8/2013 Spiegler et al.
2013/0211952 A1 8/2013 Sugaya
2013/0216491 A1 8/2013 Ogihara et al.
2013/0243718 A1 9/2013 Pasquet
2013/0244922 A1 9/2013 Bartelt
2013/0251659 A1 9/2013 Derks et al.
2013/0261091 A1 10/2013 Gerlach et al.
2013/0280192 A1 10/2013 Carter et al.
2013/0280202 A1 10/2013 Stella et al.
2013/0284195 A1 10/2013 Murdock
2013/0296289 A1 11/2013 Hall et al.
2014/0037703 A1 2/2014 Dihora et al.
2014/0039066 A1 2/2014 Grimadell et al.
2014/0086893 A1 3/2014 Gutmann et al.
2014/0112879 A1 4/2014 Molenda et al.
2014/0127149 A1 5/2014 Lepilleur
2014/0131395 A1 5/2014 Chang
2014/0134125 A1 5/2014 Dahl
2014/0147025 A1 5/2014 Periaswamy
2014/0161759 A1 6/2014 Meralli et al.
2014/0162979 A1 6/2014 Palla-venkata
2014/0171471 A1 6/2014 Krueger
2014/0216495 A1 8/2014 Bureiko
2014/0228268 A1 8/2014 Fahl et al.
2014/0237732 A1 8/2014 Zuedel Fernandes et al.
2014/0246515 A1 9/2014 Nakajima
2014/0308227 A1 10/2014 Mabille
2014/0309154 A1* 10/2014 Carter .................... A61K 8/604
510/119
2014/0323445 A1 10/2014 Gerlach et al.
2014/0335041 A1 11/2014 Peffly et al.
2014/0348884 A1 11/2014 Hilvert et al.
2014/0348886 A1 11/2014 Johnson et al.
2015/0010487 A1 1/2015 Snyder et al.
2015/0021496 A1 1/2015 Shabbir
2015/0037273 A1 2/2015 Wagner
2015/0050231 A1 2/2015 Murase
2015/0065476 A1 3/2015 Aistrup et al.
2015/0071977 A1 3/2015 Dihora
2015/0093420 A1 4/2015 Snyder
2015/0093429 A1 4/2015 Carter et al.
2015/0098921 A1 4/2015 Franzke et al.
2015/0099684 A1 4/2015 Boutique
2015/0110728 A1 4/2015 Jayaswal
2015/0147286 A1 5/2015 Barrera
2015/0218496 A1 8/2015 Schmiedel et al.
2015/0262354 A1 9/2015 Periaswamy
2015/0297489 A1 10/2015 Kleinen et al.
2015/0299400 A1 10/2015 Wagner et al.
2015/0313818 A1 11/2015 Stagg
2015/0313819 A1 11/2015 Edelson
2015/0359725 A1 12/2015 Glenn, Jr. et al.
2015/0359726 A1 12/2015 Glenn, Jr. et al.
2015/0359728 A1 12/2015 Glenn, Jr. et al.
2016/0008257 A1 1/2016 Zhou et al.
2016/0022566 A1 1/2016 Figura
2016/0095807 A1 4/2016 Stella et al.

(56) References Cited

U.S. PATENT DOCUMENTS

| | | | |
|---|---|---|---|
| 2016/0113849 | A1 | 4/2016 | Grimadell et al. |
| 2016/0128944 | A1 | 5/2016 | Chawrai |
| 2016/0193125 | A1 | 7/2016 | Jones et al. |
| 2016/0235643 | A1 | 8/2016 | Mathonneau et al. |
| 2016/0250137 | A1 | 9/2016 | Noor et al. |
| 2016/0279041 | A1 | 9/2016 | Hloucha |
| 2016/0279048 | A1 | 9/2016 | Jayaswal et al. |
| 2016/0287503 | A1 | 10/2016 | Schroeder |
| 2016/0287509 | A1 | 10/2016 | Peffly |
| 2016/0303043 | A1 | 10/2016 | Khoury |
| 2016/0309871 | A1 | 10/2016 | Torres Rivera et al. |
| 2016/0310369 | A1 | 10/2016 | Thompson et al. |
| 2016/0310370 | A1 | 10/2016 | Zhao et al. |
| 2016/0310371 | A1 | 10/2016 | Zhao |
| 2016/0310375 | A1 | 10/2016 | Torres Rivera |
| 2016/0310386 | A1 | 10/2016 | Smith, III et al. |
| 2016/0310388 | A1 | 10/2016 | Smith, III et al. |
| 2016/0310389 | A1 | 10/2016 | Thompson et al. |
| 2016/0310390 | A1 | 10/2016 | Smith, III et al. |
| 2016/0310391 | A1 | 10/2016 | Smith, III et al. |
| 2016/0310393 | A1 | 10/2016 | Chang |
| 2016/0310402 | A1 | 10/2016 | Zhao et al. |
| 2016/0317424 | A1 | 11/2016 | Kadir |
| 2016/0346184 | A1 | 12/2016 | Schwartz et al. |
| 2016/0354300 | A1 | 12/2016 | Thompson et al. |
| 2017/0071837 | A1 | 3/2017 | Schelges et al. |
| 2017/0101609 | A1 | 4/2017 | Vargas |
| 2017/0110690 | A1 | 4/2017 | Lamansky et al. |
| 2017/0110695 | A1 | 4/2017 | Nishikawa et al. |
| 2017/0135932 | A1 | 5/2017 | Schwartz et al. |
| 2017/0165164 | A1 | 6/2017 | Zhao et al. |
| 2017/0165165 | A1 | 6/2017 | Zhao et al. |
| 2017/0209359 | A1 | 7/2017 | Zhao et al. |
| 2017/0225006 | A1 | 8/2017 | Anderson |
| 2017/0239155 | A1 | 8/2017 | Hartnett |
| 2017/0252273 | A1 | 9/2017 | Renock et al. |
| 2017/0278249 | A1 | 9/2017 | Stofel |
| 2017/0283959 | A1 | 10/2017 | Shellef |
| 2017/0304172 | A1 | 10/2017 | Chang et al. |
| 2017/0304184 | A1 | 10/2017 | Glenn, Jr. |
| 2017/0304185 | A1 | 10/2017 | Glenn, Jr. et al. |
| 2017/0304186 | A1 | 10/2017 | Glenn, Jr. |
| 2017/0333321 | A1 | 11/2017 | Carnali |
| 2018/0044097 | A1 | 2/2018 | Zeik |
| 2018/0057451 | A1 | 3/2018 | Owens et al. |
| 2018/0110594 | A1 | 4/2018 | Atkin |
| 2018/0110688 | A1 | 4/2018 | Torres Rivera et al. |
| 2018/0110689 | A1 | 4/2018 | Torres Rivera et al. |
| 2018/0110690 | A1 | 4/2018 | Torres Rivera |
| 2018/0110691 | A1 | 4/2018 | Torres Rivera et al. |
| 2018/0110692 | A1 | 4/2018 | Torres Rivera et al. |
| 2018/0110693 | A1 | 4/2018 | Renock et al. |
| 2018/0110694 | A1 | 4/2018 | Renock et al. |
| 2018/0110695 | A1 | 4/2018 | Thompson |
| 2018/0110696 | A1 | 4/2018 | Johnson et al. |
| 2018/0110704 | A1 | 4/2018 | Zhao et al. |
| 2018/0110707 | A1 | 4/2018 | Zhao et al. |
| 2018/0110710 | A1 | 4/2018 | Zhao et al. |
| 2018/0110714 | A1 | 4/2018 | Glenn, Jr. et al. |
| 2018/0116937 | A1 | 5/2018 | Park et al. |
| 2018/0116941 | A1 | 5/2018 | Wang |
| 2018/0221266 | A1 | 8/2018 | Zhao et al. |
| 2018/0256481 | A1 | 9/2018 | Glenn, Jr. |
| 2018/0311135 | A1 | 11/2018 | Chang et al. |
| 2018/0311136 | A1 | 11/2018 | Chang |
| 2018/0318194 | A1 | 11/2018 | Hoffmann et al. |
| 2018/0325791 | A1 | 11/2018 | Lane et al. |
| 2018/0344598 | A1 | 12/2018 | Punyani |
| 2018/0344611 | A1 | 12/2018 | Zhao et al. |
| 2018/0344612 | A1 | 12/2018 | Zhao et al. |
| 2018/0344613 | A1 | 12/2018 | Zhao et al. |
| 2018/0344614 | A1 | 12/2018 | Zhao et al. |
| 2019/0021971 | A1 | 1/2019 | Schroeder |
| 2019/0105242 | A1 | 4/2019 | Song |
| 2019/0105243 | A1 | 4/2019 | Song et al. |
| 2019/0105244 | A1 | 4/2019 | Song |
| 2019/0105245 | A1 | 4/2019 | Song |
| 2019/0105246 | A1 | 4/2019 | Cochran |
| 2019/0105247 | A1 | 4/2019 | Song |
| 2019/0117543 | A1 | 4/2019 | Zhao |
| 2019/0117544 | A1 | 4/2019 | Zhao |
| 2019/0117545 | A1 | 4/2019 | Zhao |
| 2019/0142711 | A1 | 5/2019 | Torres Rivera |
| 2019/0167554 | A1 | 6/2019 | Wankhade |
| 2019/0183777 | A1 | 6/2019 | Gillis |
| 2019/0183778 | A1 | 6/2019 | Glenn, Jr. |
| 2019/0192405 | A1 | 6/2019 | Zhao |
| 2019/0240121 | A1 | 8/2019 | Torres Rivera |
| 2019/0307298 | A1 | 10/2019 | Zhao |
| 2019/0313637 | A1 | 10/2019 | Seelmann-eggebert et al. |
| 2019/0328641 | A1 | 10/2019 | Kelada |
| 2019/0328647 | A1 | 10/2019 | Chang et al. |
| 2019/0365633 | A1 | 12/2019 | Glenn, Jr. |
| 2019/0381055 | A1 | 12/2019 | Cong |
| 2020/0000690 | A1 | 1/2020 | Renock et al. |
| 2020/0061018 | A1 | 2/2020 | Lawyer et al. |
| 2020/0129402 | A1 | 4/2020 | Jamadagni |
| 2020/0163334 | A1 | 5/2020 | Albright et al. |
| 2020/0163846 | A1 | 5/2020 | Song |
| 2020/0163905 | A1 | 5/2020 | Mendrok-edinger et al. |
| 2020/0237628 | A1 | 7/2020 | Torres Rivera |
| 2020/0323766 | A1 | 10/2020 | Minou et al. |
| 2021/0022986 | A1 | 1/2021 | Glenn, Jr. |
| 2021/0030659 | A1 | 2/2021 | Stebbins |
| 2021/0069091 | A1 | 3/2021 | Oh et al. |
| 2021/0128419 | A1 | 5/2021 | Stebbins et al. |
| 2021/0186839 | A1 | 6/2021 | Kroger Lyons et al. |
| 2021/0283131 | A1 | 9/2021 | Richards et al. |
| 2021/0401707 | A1 | 12/2021 | Johnson et al. |
| 2021/0401710 | A1 | 12/2021 | Johnson et al. |
| 2021/0401818 | A1 | 12/2021 | Richards et al. |
| 2022/0160606 | A1 | 5/2022 | Renock |
| 2022/0202677 | A1 | 6/2022 | Stephens et al. |
| 2024/0108567 | A1 | 4/2024 | Punyani |

FOREIGN PATENT DOCUMENTS

| | | | |
|---|---|---|---|
| CN | 1298293 | A | 6/2001 |
| CN | 1917853 | A | 2/2007 |
| CN | 102715187 | A | 10/2012 |
| CN | 102895151 | A | 1/2013 |
| CN | 102697668 | B | 8/2013 |
| CN | 103356408 | A | 10/2013 |
| CN | 103655415 | A | 3/2014 |
| CN | 102697670 | B | 7/2014 |
| CN | 102851015 | B | 12/2014 |
| CN | 104244922 | A | 12/2014 |
| CN | 104302705 | A | 1/2015 |
| CN | 104755138 | A | 7/2015 |
| CN | 105007884 | A | 10/2015 |
| CN | 105555252 | A | 5/2016 |
| CN | 105636649 | A | 6/2016 |
| CN | 105726393 | A | 7/2016 |
| CN | 105769617 | A | 7/2016 |
| CN | 104000749 | B | 9/2016 |
| CN | 106659673 | A | 5/2017 |
| CN | 106750361 | A | 5/2017 |
| CN | 107072927 | A | 8/2017 |
| CN | 107126409 | A | 9/2017 |
| CN | 109620896 | A | 4/2019 |
| CN | 109700877 | A | 5/2019 |
| CN | 109757493 | A | 5/2019 |
| CN | 105434465 | B | 7/2019 |
| CN | 110025658 | A | 7/2019 |
| CN | 110420131 | A | 11/2019 |
| CN | 109745261 | B | 9/2021 |
| DE | 4315396 | A1 | 11/1994 |
| DE | 202005009618 | U1 | 9/2005 |
| DE | 102007050371 | A1 | 4/2009 |
| DE | 102008050430 | A1 | 4/2010 |
| DE | 102011000927 | A1 | 8/2012 |
| DE | 102015204987 | A1 | 9/2016 |
| EP | 0574086 | A2 | 12/1993 |
| EP | 0674898 | A2 | 10/1995 |

(56) References Cited

FOREIGN PATENT DOCUMENTS

| | | | |
|---|---|---|---|
| EP | 0753558 | A1 | 1/1997 |
| EP | 0996410 | A1 | 5/2000 |
| EP | 1340485 | A2 | 2/2003 |
| EP | 1346720 | A2 | 9/2003 |
| EP | 0674898 | B2 | 3/2006 |
| EP | 1714678 | A1 | 10/2006 |
| EP | 2786742 | A1 | 10/2014 |
| EP | 2042216 | B1 | 9/2015 |
| JP | S56011009 | A | 12/1981 |
| JP | S58113300 | A | 7/1983 |
| JP | S61236708 | A | 10/1986 |
| JP | H04364114 | A | 12/1992 |
| JP | 07252134 | A | 10/1995 |
| JP | H08310924 | A | 11/1996 |
| JP | 09030938 | A | 2/1997 |
| JP | H09143087 | A | 6/1997 |
| JP | H09175961 | A | 7/1997 |
| JP | 2964226 | B2 | 10/1999 |
| JP | 3069802 | B2 | 7/2000 |
| JP | 2003201217 | A | 12/2001 |
| JP | 2002179552 | A | 6/2002 |
| JP | 2002193766 | A | 7/2002 |
| JP | 2002226889 | A | 8/2002 |
| JP | 2003055699 | A | 2/2003 |
| JP | 3480165 | B2 | 12/2003 |
| JP | 3634988 | B2 | 3/2005 |
| JP | 3634991 | B2 | 3/2005 |
| JP | 3634996 | B2 | 3/2005 |
| JP | 2005187359 | A | 7/2005 |
| JP | 2005232113 | A | 9/2005 |
| JP | 2006124312 | A | 5/2006 |
| JP | 2006183039 | A | 7/2006 |
| JP | 2006193549 | A | 7/2006 |
| JP | 2007131687 | A | 5/2007 |
| JP | 2008001626 | A | 1/2008 |
| JP | 2008214292 | A | 9/2008 |
| JP | 2009057387 | A | 3/2009 |
| JP | 2009096778 | A | 5/2009 |
| JP | 2010511693 | A | 4/2010 |
| JP | 2010275198 | A | 12/2010 |
| JP | 2011508728 | A | 3/2011 |
| JP | 2011153167 | A | 8/2011 |
| JP | 2011190221 | A | 9/2011 |
| JP | 5041113 | B2 | 7/2012 |
| JP | 2013010757 | A | 1/2013 |
| JP | 2013091641 | A | 5/2013 |
| JP | 2013133319 | A | 7/2013 |
| JP | 2013151434 | A | 8/2013 |
| JP | 6046394 | B2 | 1/2014 |
| JP | 2014024875 | A | 2/2014 |
| JP | 2014091723 | A | 5/2014 |
| JP | 5667790 | B2 | 2/2015 |
| JP | 2015101545 | A | 6/2015 |
| JP | 2015205834 | A | 11/2015 |
| JP | 2018012673 | A | 1/2018 |
| JP | 2018511638 | A | 4/2018 |
| KR | 20050031235 | A | 4/2005 |
| KR | 1020080111280 | A | 12/2008 |
| KR | 1020120018739 | A | 3/2012 |
| KR | 20140060882 | A | 5/2014 |
| WO | 9114759 | A1 | 10/1991 |
| WO | 91017237 | A1 | 11/1991 |
| WO | 9502389 | A2 | 1/1995 |
| WO | 9527471 | A1 | 10/1995 |
| WO | 9726854 | A1 | 7/1997 |
| WO | 9823258 | A1 | 6/1998 |
| WO | 9913823 | A2 | 3/1999 |
| WO | 9918928 | A1 | 4/1999 |
| WO | 9924004 | A1 | 5/1999 |
| WO | 9924013 | A1 | 5/1999 |
| WO | 0012553 | A1 | 3/2000 |
| WO | 0069410 | A1 | 11/2000 |
| WO | 0142409 | A1 | 6/2001 |
| WO | 0148021 | A1 | 7/2001 |
| WO | 0174312 | A2 | 10/2001 |
| WO | 0200027 | A1 | 1/2002 |
| WO | 02100360 | A1 | 12/2002 |
| WO | 2004043414 | A1 | 5/2004 |
| WO | 2004078901 | A1 | 9/2004 |
| WO | 2005023975 | A1 | 3/2005 |
| WO | 2005074868 | A1 | 8/2005 |
| WO | 2007001844 | A1 | 1/2007 |
| WO | 2008145582 | A1 | 12/2008 |
| WO | 2009016555 | A2 | 2/2009 |
| WO | 2009053931 | A2 | 4/2009 |
| WO | 2010052147 | A2 | 5/2010 |
| WO | 2012017091 | A2 | 2/2012 |
| WO | 2012040804 | A2 | 4/2012 |
| WO | 2012055587 | A1 | 5/2012 |
| WO | 2012058557 | A2 | 5/2012 |
| WO | 2012084970 | A1 | 6/2012 |
| WO | 2012117828 | A1 | 9/2012 |
| WO | 2012130644 | A1 | 10/2012 |
| WO | 2013010706 | A2 | 1/2013 |
| WO | 2013050241 | A1 | 4/2013 |
| WO | 2014073245 | A1 | 5/2014 |
| WO | 2014148245 | A1 | 9/2014 |
| WO | 2014165253 | A1 | 10/2014 |
| WO | 2015090742 | A1 | 6/2015 |
| WO | 2015122371 | A1 | 8/2015 |
| WO | 2016058837 | A1 | 4/2016 |
| WO | 2016147196 | A1 | 9/2016 |
| WO | 2017009206 | A1 | 1/2017 |
| WO | 2017042004 | A1 | 3/2017 |
| WO | 2017052161 | A1 | 3/2017 |
| WO | 2017140798 | A1 | 8/2017 |
| WO | 2018023180 | A1 | 2/2018 |
| WO | 2018075831 | A1 | 4/2018 |
| WO | 2018200646 | A1 | 11/2018 |
| WO | 2019166521 | A1 | 9/2019 |
| WO | 2020264577 | A1 | 12/2020 |
| WO | 2023097435 | A1 | 6/2023 |
| WO | 2023097438 | A1 | 6/2023 |
| WO | 2023230018 | A1 | 11/2023 |

OTHER PUBLICATIONS

"Soda Shampoo", Mintel Database, dated Apr. 2015; pp. 1-4.

"Treatment Foam for Recurrent Scaling Conditions", Mintel Database, Aug. 2007; pp. 1-2.

1999 Cosmetic Ingredient Review Summary, compiled by China Fragrance, Flavor and Cosmetics Industry Association, China Light Industry Press, publication date: Apr. 30, 2000, p. 168.

All Office Actions; U.S. Appl. No. 18/599,554, filed Mar. 8, 2024.

All Office Actions; U.S. Appl. No. 18/599,579, filed Mar. 8, 2024.

Andrew J. Wiemer et al., "A live imaging cell motility screen identifies prostaglandin E 2 as a T cell stop signal antagonist", The Journal of Immunology, vol. 187, No. 7, Oct. 1, 2011, 9 pgs.

Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018 ; 1 page.

Anonymous: "Mixtures of fungicides and insecticides", Research disclosure, Kenneth Mason Publications, Hampshire UK, GB, vol. 338, No. 93, Jun. 1, 1992, 9 pgs.

Balzer et al., Viscoelasticity of personal care products, Colloids and Surfaces A: Physicochemical and Engineering Aspects 99 , Feb. 23, 1995, pp. 233-246.

C. C. Zouboulis et al. "Acne is an inflammatory disease and alterations of sebumcomposition initiate acne lesions", J Eur Acad Dermatol Venereol, 2014, vol. 28, Issue5, pp. 527-532.

Carbopol Aqua SF-1 Polymer Technical Data Sheet, TDS-294, dated Dec. 2000 ; pp. 1-9.

Christensen et al., "Experimental Determination of Bubble Size Distribution in a Water col. by Interferometric Particle Imaging and Telecentric Direct Image Method", Student Report, Aalborg University; dated Jun. 3, 2014; 123 pages.

Crothix: High Performance Thickener, Personal Care, Croda Inc, Sep. 11, 2014, pp. 1-9.

D'Souza et al., Shampoo and Conditioners: What a Dermatologist Should Know? Indian J Dermatol, dated May-Jun. 2015; pp. 60(3), 248-254 (2015).

(56) References Cited

OTHER PUBLICATIONS

Dehyquart Guar: Published dated Nov. 2010 ; pp. 1-34.
Fevola, Michael J. "Guar Hydroxypropyltrimonium Chloride." Cosmetics and toiletries; vol. 127.1; Jan. 2012 ; pp. 16-21.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Hyun Seung Wi et al., "The anti-fungal effect of light emitting diode on yeasts", Journal of Dermatological Science, vol. 67, No. 1, Apr. 4, 2012, pp. 3-8.
Inspection certificate for Hostapon® CCG, Clariant Ibérica Production, S.A., May 6, 2019; p. 1-2.
K. J. Mills et al. "Dandruff/seborrhoeic dermatitis is characterized by aninflammatory genomic signature and possible immunedysfunction: transcriptional analysis of the condition andtreatment effects of zinc pyrithione", British Journal of Dermatology, 2012 vol. 166, pp. 33-40.
Medvedev, Diffusion Coefficients in Multicomponent Mixtures, PHD Thesis from Technical University of Denmark, dated 2005, 181 pages.
Musazzi, "Emulsion versus nonoemulsion: how much is the formulative shift critical for a cosmetic product?" (Drug Deliv. and Trans. Res. (2018) 8: pp. 414-421 (Year: 2018).
P. Mondon et al. "Reinforcement of barrier function and scalp homeostasis by Senkyunolide A to fight against dandruff", International Journal of Cosmetic Science, 2017, vol. 39, pp. 617-621.
Parchem fine & specialty chemicals. MIPA-laureth sulfate supplier distributor—CAS 83016-76-6; dated 2021; pp. 1-7.
Paterson "Salicylic acid: a link between aspirin, diet and the prevention of colorectal cancer", QJM, Aug. 2001, vol. 94(8); pp. 2.
Perm Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Pierard-Franchimont C et al: "Effect ofresidence time on the efficacy of antidandruff shampoos", International Journal of Cosmetic Science,Jun. 30, 2003 (Jun. 30, 2003), XP055794760, DOI: 10.IIII/j.1467-2494.2003.00195.x Retrieved from the Internet: URL:https://doi.org/10.IIII/j.1467-2494.2003.00195.x[retrieved on Apr. 13, 2021] "Introduction" 6 pgs.
Pierard-Franchimont C., et al., "Revisiting dandruff", International Journal of Cosmetic Science, Kluwer Academic Publishers, Dordrecht, NL, vol. 28, No. 5, Oct. 1, 2006, pp. 311-318.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Sheet for Chemoryl LS Surfactant, Sodium Lauroyl Sarcosinate, Lubrizol Advanced Materials, Inc., Mar. 24, 2020; 1-2 pages.
Product Data Sheet, Eversoft UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
Robinson et al., Final Report of the Amended Safety Assessment of Sodium Laureth Sulfate and Related Salts of Sulfated Ethoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Schwartz et al. ("Shampoos for Normal Scalp Hygiene and Dandruff" Cosmetic Dermatology. Oxford, UK: Wiley-Blackwell, 2010. 115-122. Web). (Year: 2010).
Turner et al. "Stratum Corneum Dysfunction in Dandruff", International Journal of Cosmetic Science, 34, Feb. 24, 2012, pp. 298-306.
Unpublished U.S. Appl. No. 18/599,554, filed Mar. 8, 2024, to Brennan Alexander Schilling et al.
Unpublished U.S. Appl. No. 18/599,579, filed Mar. 8, 2024, to Brennan Alexander Schilling et al.
UL Prospector® Product Data Sheet, Plantacare® 818 UP, C8-16 fatty alcohol glucoside, BASF, dated May 21, 2015; 1-3 pages.
"Deep Image Matting", Ning Xu et al., Beckman Institute for Advanced Science and Technology, University of Illinois at Urbana-Champaign, Adobe Research, dated Mar. 10, 2017; 10 pages.
Anon et al., "Journal of the American College of Toxicology," In Journal of the American College of Toxicology, vol. 7, No. 3, XP093408184, Mar. 31, 1988, pp. 335-351.
Anonymous: "Polyquaternium-10—Surfactant—SAAPedia—Surfactant Technology Platform", Retrieved from the Internet: URL: http://https//www.surfactant.top/en/saa/?type=detail&id=3743, XP93044140, May 3, 2023, 4 Pages.

* cited by examiner

REDUCTION OF OIL TRANSFER FROM SCALP TO HAIR WITH INCREASING POLARITY OF HAIR

FIELD

The present invention relates to a hair care composition for reducing oil transfer from scalp to hair.

BACKGROUND

Scalp's oils affect many aspects of scalp and hair physiology as well as satisfaction with hair's look and feel. Perception of unwanted hair oiliness is impacted by several endogenous factors such as scalp type, hair type, hormones, age, diet, and exogenous factors such as hair care products, climate, and lifestyle. While today's shampoo products are designed to remove oil, people often feel dissatisfied with the length of time their hair feels clean. Shampoos do not typically affect the transfer of scalp oils from scalp to hair, which happens throughout the day and night. It has not been found that certain materials and formulations can modify the polarity of the hair surface, which helps reduce oil transfer from scalp to hair.

SUMMARY

The present application is directed to a hair care products composition comprising a material or mixtures of materials which makes hair polar wherein one or more material is selected from synthetic or naturally derived hydrophilic polymers and/or cationic surfactants. The hair care composition can comprise about 0.05% to 5% of a hydrophilic polymer selected from the group consisting of polyvinylalcohols and derivatives, polyacrylates ethers, polyvinyl pyrrolidones, polyvinyl pyrrolidones copolymer (vinylpyrrolidone/dimethylaminoethylmethacrylate), vinyl cyanides, vinyl phosphates, vinyl phosphonates, vinyl sulfates, vinyl sulfonates, polyethylenimine and other polyamines, cellulose, collagen, polyethylene glycols and polycarboxylate co-polymers of maleic/olefin and mixtures thereof; wherein the hair care composition provides a water contact angle of les than 85 to hair. The total lipid value on hair decreases when compared to a control, the total lipid value on hair is less than 0.15 when measured using Fourier-Transform Infra-red spectroscopy (FTIR).

DETAILED DESCRIPTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions herein can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the composition onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Rinse-off" in reference to compositions, means compositions intended to be applied to keratinous substrate and subsequently removed by washing, rinsing or wiping within a few minutes or less from the application. These "rinse-off" compositions are to be distinguished from "leave-on" compositions, which are intended to be applied to and allowed to remain longer on the keratinous tissue.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 5 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M. Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for use herein. Except if stated otherwise, the term "polymer" used herein includes any type of polymer including homopolymers and copolymers.

The mechanism of action for reducing oil transfer from scalp to hair involves surface modification of hair surface, creating polar surface (hydrophilic, high surface energy, lower water contact angle on hair). As hair growing out of scalp is hydrophobic in nature, after shower using a typical cleansing shampoo or hair products it retains same degree of hydrophobicity or increase in in hydrophobicity due to deposition of conditioning ingredients such as silicone, fatty alcohol. During the day and night, before the next wash the oil continuously transfer from scalp to hair and higher hydrophobic hair leads to more and faster oil transfer from scalp to hair. Currently technologies have been focusing on removing oil, reducing oil secretion from sebaceous glands which doesn't stop hair gets greasy during the day and night, as oil keep transferring from scalp to hair. Accordingly, it would be desirable to incorporate hydrophilic polymer(s) and/or cationic surfactant(s) into hair compositions to modify the polarity of the hair surface and help reduce oil transfer from the scalp to the hair. Reducing oil transfer improves hair feel by reducing or eliminating the greasy or oily feeling. This method of treatment makes hair cleaner longer achieved by making hair surface polar and reducing oil transfer from scalp to hair. Degree of hydrophilicity on hair can be determined by measuring water contact angle measurement with a mobile surface analyzer (MSA), which is a known technique in the art. The amount of oil reduction on hair can be measured using Fourier-Transform Infra-red spectroscopy (FTIR) as total lipids ($CH_2$), triglycerides, fatty acids or using a sebumeter, which is a known technique in the art.

A. Hydrophilic Polymers

The hydrophilic polymer can be synthetic or naturally derived, can be one polymer or a mixture of two or more polymer or a copolymer with another polymeric unit. Hydrophilic polymers can include, but are not limited to, polyacrylates (and esters), other functionalized polyolefins, (such as PVA (polyvinyl alcohols and esters), PVA ethers, PVP (vinyl pyrrolidones), PVP copolymer (vinylpyrrolidone/dimethylaminoethylmethacrylate), vinyl cyanides, phosphates, phosphonates, sulfates, sulfonates, etc. polyethylenimine and other polyamines, polyethylene glycols and polycarboxylate co-polymers of maleic/olefin. The olefin segment may include a variety of linear, branched and cyclic alkenes. Suitable alkenes may include or be derived from propylene, ethylene, or butylenes. Particularly suitable alkenes may include or be derived from butylene, for example, isobutylene and diisobutylene. The hydrophilic polymer may have a cationic charge. The hydrophilic polymer may be polyquaterniu-10, such as UCARE Extreme Polymer supplied by Dow Inc., or may be cetyl hydroxyethylcellulose, such as Polysurf 67 CS or Natrosol 330 PLUS CS, both supplied by Ashland. Other suitable polymeric agents include silicone materials such as polydimethysiloxane materials (e.g., Wacker HC303 from Wacker Silicones), fluorinated acrylic copolymer e.g., Capstone ST100 and ST300 from Dupont), polycarboxylate copolymers (e.g., Acusol 460 from Dow), and acrylic polymers (Polyquart® Pro A from BASF, Rhoplex EZ Clean 200 from Dow, Polyquart® Pro, Polyquart® Ampho 149, and Polyquart® EcoClean from Cognis) and other polyethers, poly(styrene maleic anhydride), polyesters, polyureas, polyurethanes, polycarbonates, polyacrylamides, sugars and polymeric analogs, chitosan, collagen, tapioca starch and derivatives thereof. The hydrophilic polymer may be selected from PVP copolymer (Vinylpyrrolidone/Dimethylaminoethylmethacrylate), mono-long alkyl amidoamine salt or mixtures thereof. The hydrophilic polymer may be included in the composition at a level by weight of from about 0.05% to about 5%, or from about 0.05% to about 3%, or from about 0.1% to about 2%, and/or from about 0.2% to about 1%.

B. Cationic Surfactant

The cationic surfactant can be one cationic surfactant or a mixture of two or more cationic surfactants. The cationic surfactant may be selected from mono-long alkyl quaternized ammonium salt, di-long alkyl quaternized ammonium salt, mono-long alkyl amidoamine salt or mixtures thereof. The cationic surfactant system can be included in the composition at a level by weight of from about 0.1% to about 10%, from about 0.5% to about 8%, from about 0.8% to about 5%, and from about 1.0% to about 4%.

The mono-long alkyl quaternized ammonium salt cationic surfactants useful herein are those having one long alkyl chain which has from about 12 to about 30 carbon atoms, or from about 16 to about 24 carbon atoms, and/or from about 18 to about 22 carbon atoms. The remaining groups attached to the nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. The counterion is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Nonlimiting examples of such mono-long alkyl quaternized ammonium salt cationic surfactants include: behenyl trimethyl ammonium salt.

The di-long alkyl quaternized ammonium salt cationic surfactants useful herein are those having two long alkyl chains of from 12 to 30 carbon atoms, or from 16 to 24 carbon atoms, or from 16 to 22 carbon atoms or an aromatic, alkoxy, polyoxyalkylene, alkylamido, hydroxyalkyl, aryl or alkylaryl group having up to about 30 carbon atoms. The remaining substituents on the nitrogen atom are selected from an aliphatic group of from 1 to about 8 carbon atoms, or from 1 to 3 carbon atoms or an aromatic, alkoxy, polyoxyalkylene, alkylamido, hydroxyalkyl, aryl or alkylaryl group having up to about 8 carbon atoms. The counterion is a salt forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Nonlimiting examples of di-long alkyl cationic surfactants include dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide Materials may be chosen from hydrophilic polymers such as PVP, Polyquart Pro A, sodium hyaluronate and/or cationic surfactant such as stearamidopropyldimethylamine can also be used in the combination to increase the size of the benefit.

The concentration of the hydrophilic polymer in the present hair care product compositions may be from about 0.05% to 5%, or from about 0.05% to about 3%, or from about 0.1% to about 2%, and/or from about 0.2% to about 1%.

| Name (0.3% in ethanol:water) | Total Lipid measured on Hair ($CH_2$ using FTIR) | Water contact angle on Hair (deg using MSA) |
|---|---|---|
| Oily hair (no treatment) | 0.114 | 92.6 |
| Ethanol:Water (1:1, vehicle only) | 0.113 | 85.7 |
| PVP copolymer[1](vinylpyrrolidone/dimethylaminoethyl methacrylate) | 0.082 | 54.9 |
| Acrylic copolymer sodium salt[2] | 0.103 | 59.8 |
| Collagen[3] | 0.097 | 82 |

[1]Copolymer 845-O (PVP copolymer), Ashland
[2]Polyquart® Pro A, BASF
[3]Gelatin Novotec® CB800, Gelita The Total Lipid on hair is measured using FTIR wherein it detects the vibration of $CH_2$ backbone as lipid group. $CH_2$ is the lipid functional group $CH_2$ carbon-hydrogen backbone.

The hair care composition may provide a water contact angle of <85 to hair, may provide a water contact angle of <80 to hair, or may provide a water contact angle of <75 to hair.

The hair care composition may provide a decrease in total lipid value on hair compared to a control. The hair care composition may provide a total lipid value on hair which is less than 0.15 (e.g., less than 0.11 or even less than 0.09) when measured using Fourier-Transform Infra-red spectroscopy (FTIR) as total lipids ($CH_2$).

The cationic surfactant system can be included in the composition at about 0.1% to about 10%, (e.g., 0.5% to 8%, 0.8% to 5%, or even 1.0% to 4%).

| Name (2% in aqueous solution) | % Sebum transferred measured on hair using sebumeter | Water contact angle on Hair (degree using MSA) |
|---|---|---|
| Oily hair (no treatment) | 100% | 94 |
| Water (vehicle only) | 85% | 88 |
| Stearamidopropyl-dimethylamine[1] | 56% | 71 |
| Benzyltriethylammonium chloride[2] | 65% | 78 |
| Behenamidopropyl dimethylamine[3] | 72% | 80 |

-continued

[1]Genamin SPA, Clariant KCI Ltd.
[2]SAPDMA, KCI, Ltd.
[3]KCI Ltd.

FORMULATIONS AND EXAMPLES

The following are non-limiting examples. The examples are given solely for the purpose of illustration and are not to be construed as limitations, as many variations thereof are possible without departing from the spirit and scope of the invention, which would be recognized by one of ordinary skill in the art.

Formulation Preparation and Treatment Protocols to Evaluate the Effectiveness of Hydrophilic Polymers and Cationic Surfactant Leave-On Treatment Composition Preparation:

The leave-on treatment compositions are prepared by adding the hydrophilic polymers and perfume, if needed, into ethanol/water carrier and stirred until complete dissolution. The solution pH is adjusted using sodium hydroxide (50% w/w) or citric acid to a final pH of 4.0-6.0. The Sepimax® Zen is then added, if needed, and the solution is mixed using a high-speed-mixer for 2-5 minutes at 1800-2300 rpm until a uniform composition is obtained.

Leave-On Hair Treatment Protocol:

An amount of 0.20 g of each composition of Examples Ito IV is spread via a syringe onto separate natural virgin brown hair switches weighing 2.0 g (dosage 0.10 g of solution per g of hair). The hair is allowed to air dry and then oil is transferred from scalp mimic using the oil transfer method described above. The oil on hair surface is then measured using FTIR or sebumeter.

Shampoo Composition Preparation:

The shampoo composition delivers consumer desired shampooing in addition to preventing oil transfer from scalp to hair.

The shampoo composition comprises from about 0.01% to about 5%, alternatively from about 0.05% to about 3%, alternatively from about 0.1% to about 2% of a compound selected from the group consisting of hydrophilic polymers and mixtures thereof, by weight of the shampoo composition. After applying to the hair a shampoo composition as described herein, the method then comprises rinsing the shampoo composition from the hair.

Shampoo Hair Treatment Protocol:

All testing are performed on Virgin Caucasian Hair weighing approximately 2.0 grams and having a length of approximately 6 inches. The hair switches are commercially available from IHIP (International Hair Importers). Three hair switches 1 per rinse-off compositions per dosage are used. Each hair switch is washed with clarifying shampoo followed by a treatment with the rinse-off conditioner according to the following protocol. An amount of 0.20 g of shampoo is spread via a syringe onto separate hair switch. That is, the dosage is 0.10 g of shampoo per g of hair. Each application consists of adding shampoo to the hair, milking for 30 seconds followed by rinsing for 30 seconds. Excess water is squeezed from the hair switches.

Rinse-Off Treatment Composition Preparation:

The rinse-off treatment compositions can be prepared by any conventional method well known in the art. The cationic surfactants and the fatty alcohols are mixed together and heated to from about 66° C. to about 85° C. to form an oil phase. Separately, the disodium EDTA, the methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

Rinse-Off Hair Treatment Protocol:

All testing are performed on Virgin Caucasian hair switches weighing approximately 2.0 grams and having a length of approximately 6 inches. The hair switches are commercially available from IHIP (International Hair Importers). Three hair switches per rinse-off compositions per dosage are used. Each hair switch is washed with clarifying shampoo followed by a treatment with the rinse-off conditioner according to the following protocol.

An amount of 0.20 g of clarifying shampoo is spread via a syringe onto separate hair switch. That is, the dosage is 0.10 g of shampoo per g of hair. Each application consists of adding shampoo to the hair, milking for 30 seconds followed by rinsing for 30 seconds. Excess water is squeezed from the hair switches and then 0.1 g/g of the rinse off hair treatment is applied and milked for 30 seconds and left on hair to rest for 15 minutes and then rinsed off with water for 30 seconds.

Oil Transfer from Scalp Mimic to Hair Switch:

Rectangular Scalp surface mimic (Bio Skin Plate #F-1, made of polyurethane elastomer material, length 192 mm, Width 129 mm, thickness 5 mm from Ohken Co., Ltd. Japan) is procured and washed with 15% SLS aqueous solution and air dried. 0.38 g of artificial sebum (from Advanced testing laboratories, Cincinnati) is applied using a finger glove and spread completely with light pressure to cover the full area of scalp mimic. The hair with treatment or without treatment is placed on scalp mimic and another scalp mimic is placed on top of hair switch, so that hair switch gets sandwiched between two scalp mimics. A gentle pressure for 5 seconds is applied and then hair is used to make measurement of oil transferred on hair from scalp mimic using FTIR or sebumeter (SEBUMETER® SM 815, Courage+Khazaka electronic GmbH). The % amount of oil transferred from scalp mimic to hair switch is calculated as follows:

- A=Amount of oil measured using sebumeter on hair treated with composition containing the hydrophilic polymer and/or cationic surfactant
- B=Amount of oil measured using sebumeter on hair treated with vehicle containing no hydrophilic polymer and/or cationic surfactant $$\%\text{ oil transfer from scalp mimic to hair}=[(B-A)\times 100]/B$$

Evaluation Methods

The hair switches that are treated with the shampoo, rinse-off conditioner, scrub, leave on treatment compositions are evaluated using the following methodology after and before oil transfer using scalp mimic.

a. Fourier Transform Infra-red (FTIR) Spectroscopy Measurement

Upon braiding, the hair switches are measured on 6 different locations in the middle of the switch with mid IR ATR-FTIR (Perkin Elmer Frontier FTIR with Specac Golden Gate single bounce diamond crystal ATR accessory). The measurement range is done from 4000-600 $cm^{-1}$ in absorption mode, with 8 scans and 4 $cm^{-1}$ spectral resolution. The ATR clamping pressure is controlled using pressure torque fixed at 70 Ncm for all the hair switches measurement. The spectrums are analyzed using MATLAB based code to preprocess the spectrum and calculate total lipid that is defined as ratio of $CH_2$ stretching peak area divided by Amide 2 peak area above the individual spectrum's baseline. The preprocessing includes the baseline correction and vector normalization. Vector normalization is calculated from the average absorption value of spectrum within selected spectral ranges. The average value calculated will then be subtracted from the spectrum, which center the spectrum around absorption value=0. This is followed by calculating the sum of squares of all absorption values, and respective spectrum is divided by the square root of this sum. The vector norm of the result spectrum is 1.

$$a_m = \frac{\sum_k a(k)}{N}$$

$$a'(k) = a(k) - a_m$$

$$a''(k) = \frac{a'(k)}{\sqrt{\sum_k (a'(k))^2}}$$

$$\sum_k (a''(k))^2 = 1$$

The $CH_2$ stretching peak area is obtained from the integration area under the absorption spectrum from right edge of 2946 $cm^{-1}$ to left edge of 2837 $cm^{-1}$ and above straight-line baseline, obtained from spectrum intersection at 3000 $cm^{-1}$ and 2700 $cm^{-1}$. The amide 2 peak area is obtained from the integration area under absorption spectrum from right edge of 1580 $cm^{-1}$ to left edge of 1475 $cm^{-1}$.

b. Sebumeter Measurement

Hair Switches (2 g, 10 inches, Caucasian virgin or damaged hair supplied by International Hair Importers) is placed on a clean surface and then sebumeter (Courage and Khazaka MPA 580 or 815 console) is used, where cartridge into the console establish the blank baseline. The cartridge with opaque film is put in contact with hair for 30 seconds firmly and tightly until 30 seconds counter goes to zero. Re-insert cartridge into the console and record the oil value displayed on screen. Move to new measuring section of the cartridge by depressing the slide of the cartridge and then pulling it back up, placing it at new area on hair 1 cm away from previous measure. Calculate the amount of oil transfer as shared above.

Hair Switch Look Assessment Method: The treated hair switches are kept at room temperature, lab conditions (32-35° C., 50% RH) for 2 hrs and then ten expert graders are asked to rate each of them in terms of hair oily look based on a 5 point scale, 5 being the highest (very oily) and 1 being the lowest rating (not oily).

Formulation Examples to Evaluate the Effectiveness of Hydrophilic Polymers

Leave-On Treatment Formulation:

| Raw Material | Formula Example: Leave-on treatment Control 1 (wt./wt.)% | 2 (wt./wt.)% | 3 (wt./wt.)% | 4 (wt./wt.)% | 5 (wt./wt.)% |
|---|---|---|---|---|---|
| Distilled Water | QS | QS | QS | QS | QS |
| Ethanol[1] | 50.00 | 50.00 | 50.00 | 50.00 | 50.00 |
| PVP copolymer[2](Vinyl-pyrrolidone/Dimethylamino-ethylmethacrylate) | 0 | 0.3 | 0 | 0 | 0.15 |
| Acrylic copolymer sodium salt[3] | 0 | 0 | 0.3 | 0 | 0.15 |
| Collagen[4] | 0 | 0 | 0 | 0.3 | 0 |
| % oil transferred on hair versus Leave-on Treatment Control at dose of 0.10 g of composition for 1.0 g of hair (Lower is Better) using sebumeter | 65 | 21 | 45 | 37 | 15 |
| Rating Hair Oily look vs. Leave-on Treatment Control at dose of 0.10 g of composition for 1.0 g of hair. 5 for very oily and 1 for not oily | 4 | 2 | 3 | 3 | 1 |

[1]Alcodis (Brussels)
[2]Copolymer 845-O (PVP copolymer), Ashland
[3]Polyquart Pro A, BASF
[4]Gelatin Novotec CB800, Gelita

| Formula Example / Raw Material | 6 | 7 | 8 | 9 | 10 | 11 |
|---|---|---|---|---|---|---|
| Distilled Water | QS | QS | QS | QS | QS | QS |
| Ethanol | 25.0 | 25.0 | 50.0 | 50.0 | 50.0 | 50.0 |
| PVP copolymer[1](Vinylpyrrolidone/Dimethylaminoethylmethacrylate) | 0 | 0.25 | 0 | 0 | 0 | 0.25 |
| Acrylic copolymer sodium salt[2] | 0 | 0 | 0.25 | 0 | 0 | 0 |
| Stearamidopropyldimethylamine[3] | 0 | 0 | 0 | 1 | 0 | 0 |
| Benzyltriethylammonium chloride[4] | 0 | 0 | 0 | 0 | 1 | 0 |
| Decanediol (decylene glycol)[5] | 1.0 | 1.0 | 1.0 | 1.0 | 1.0 | 1.0 |
| Silica[6] | 3.0 | 3.0 | 3.0 | 3.0 | 3.0 | 3.0 |
| Tapioca Starch[7] | 2.0 | 2.0 | 2.0 | 2.0 | 2.0 | 2.0 |
| Sepimax Zen[8] | 0.25 | 0.25 | 0.25 | 0.25 | 0.25 | 0.25 |
| Salicylic acid[9] | 0 | 0 | 0 | 0 | 0 | 0.5 |
| Propylene glycol[10] | 0 | 0 | 0 | 0 | 0 | 0.5 |
| Piroctone Olamine[11] | 0 | 0 | 0 | 0 | 0 | 0.45 |
| Sucrose dilaurate[12] | 0.2 | 0.2 | 0.2 | 0.2 | 0.2 | 0.2 |
| Menthol[13] | 0.3 | 0.3 | 0.3 | 0.3 | 0.3 | 0.3 |
| Citric acid[14] | 0.05 | 0.05 | 0.05 | 0.05 | 0.05 | 0.05 |
| Perfume | 0.3 | 0.3 | 0.3 | 0.3 | 0.3 | 0.3 |
| Final pH | 4.5 | 4.5 | 4.5 | 4.5 | 4.5 | 4.2 |
| % oil transferred on hair versus Leave-on Treatment Control at dose of 0.10 g of composition for 1.0 g of hair (Lower is Better) using sebumeter | 47 | 20 | 27 | 35 | 40 | 15 |
| Rating Hair Oily look vs. Leave-on Treatment Control at dose of 0.10 g of composition for 1.0 g of hair. 5 for very oily and 1 for not oily | 2.7 | 2 | 2 | 2.5 | 2.5 | 1 |

[1]Copolymer 845-O (PVP copolymer), Ashland
[2]Polyquart Pro A, BASF
[3]Genamin, SPA, Clariant
[4]SAPDMA, KCI, Ltd.
[5]Symrise
[6]P&G Shiga Plant
[7]Dry Flo, Akzo Nobel
[8]Sepimax Zen, Seppic
[9]Novacyl
[10]Dow
[11]Octopirox, Clariant
[12]BASF
[13]L-Menthol Flakes, BASF
[14]Jungbunzlauer Austria Results: Formula 2 to 11 show reduction in % amount of oil transferred from scalp mimic to hair switch. Lower amount of oil are observed on hair treated with higher doses of leave-on Formulas 2 to 11. The hair oily look assessment results indicate addition of hydrophilic polymers and/or cationic surfactant results in less oily hair look versus no treatment and Example 6.

Shampoo Composition

The method of reducing oil transfer described herein comprises applying to the hair a shampoo composition. The shampoo composition delivers consumer desired cleansing and potentially conditioning. It can also deliver reducing oil transfer in the case that it contains a hydrophilic polymer. The shampoo composition may comprise from about 0.01% to about 5% hydrophilic polymers selected from the group consisting of PVP copolymer, Jaguar excel, polyquart Pro A. After applying to the hair, a shampoo composition as described herein, the method then comprises rinsing the shampoo composition from the hair.

Other Components in the Shampoo Composition

A. Detersive Surfactant

The shampoo composition comprises one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

The concentration of the surfactant in the composition should be sufficient to provide the desired cleaning and lather performance. The cleansing composition can comprise a total surfactant level of from about 6% to about 50%, from about 5% to about 35%, a total surfactant level of from about 10% to about 50%, by weight, from about 15% to about 45%, from about 15% to about 22%; from about 16% to about 20%; from about 17% to about 20%; by weight, from about 20% to about 40%, by weight, from about 22% to about 35%, and/or from about 25% to about 30%.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In some instances, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Shampoo Formulation:

| Shampoo Formula Example | Control A | B | C | D |
|---|---|---|---|---|
| Water Purified | Q.S to 100 | Q.S to 100 | Q.S to 100 | Q.S to 100 |
| Sodium Lauryl Sulfate 29% solution[1] | 20.0 | 20.0 | 20.0 | 13.0 |
| Cocamidopropyl betaine[2] | 3.5 | 3.5 | 3.5 | 0 |
| Sodium cocoyl isethionate[3] | 0 | 0 | 0 | 2.5 |
| Sodium Lauroamphoacetate[4] | 0 | 0 | 0 | 2.5 |
| Jaguar excel[5] | 0.2 | 0.2 | 0.2 | 0.2 |
| Sodium hyaluronate[6] | 0 | 0 | 0.3 | 0 |
| PVP copolymer[7](Vinylpyrrolidone/ Dimethylaminoethyl methacrylate) | 0 | 0.3 | 0 | 0 |
| Polyquaternium-10[8] | 0 | 0 | 0 | 0.2 |
| Salicylic acid[9] | 2 | 2 | 2 | 2 |
| Piroctone Olamine[10] | 0.8 | 0.8 | 0.8 | 0.8 |
| Sodium Benzoate[11] | 0.25 | 0.25 | 0.25 | 0.25 |
| Sodium Hydroxide 50% Solution[12] | 0.19 | 0.19 | 0.19 | 0.19 |
| Menthol[13] | 0.7 | 0.7 | 0.7 | 0.7 |
| Fragrance | 0.65 | 0.65 | 0.65 | 0.65 |
| % oil transferred on hair versus Shampoo Control at dose of 0.10 g of composition for 1.0 g of hair (Lower is Better) using sebumeter | 60 | 55 | 54 | 54 |
| Rating Hair Oily look vs. Shampoo Treatment Control at dose of 0.10 g of composition for 1.0 g of hair. 5 for very oily and 1 for not oily | 4 | 3 | 3 | 3 |

[1]Zhishang Huizhou Petrochemicals
[2]Dehyton KE UP, BASF
[3]Jordapon Ci-Prill, BASF
[4]Miranol Ultra L-32, Solvay
[5]Solvay
[6]P&G Shiga Plant
[7]Copolymer 845-O (PVP copolymer), Ashland
[8]UCARE Extreme Polymer from Dow Inc.
[9]Novacyl
[10]Octopirox, Clariant
[11]Emerald Kalama Chemicals
[12]Olin Chemicals, Rochester
[13]L-Menthol Flakes, BASF Results: Above table represents shampoo compositions that are used for treating hair switches. As shown in the table, hair treated with these compositions has different amount of oil transferred from scalp mimic to hair switch. Hair treated with composition of B, C and D containing hydrophilic polymers makes has less oil transferred vs. control A and are rated low on oiliness look.

Scrub Composition

Scrub composition and preparation is similar to shampoo preparation, with only addition of high salt such as sodium chloride as the last step in shampoo making.

Examples of Scrub Formula

| Material | Control E | F | G | H |
|---|---|---|---|---|
| Water | QS | QS | QS | QS |
| Sodium Lauryl Sulfate[1] | 13 | 13 | 13 | 12 |
| Sodium cocoyl isethionate[2] | 0 | 0 | 0 | 3.9 |
| Sodium Lauroamphoacetate[3] | 0 | 0 | 0 | 2.2 |
| Cocamidopropyl Betaine[4] | 2.3 | 2.3 | 2.3 | 0 |
| Glyceryl Stearate[5] | 1 | 1 | 1 | 1 |
| Menthol[6] | 0.35 | 0.35 | 0.35 | 0.35 |
| Perfume | 1.2 | 1.2 | 1.2 | 1.2 |
| Sodium hydroxide (50% solution)[7] | 0.2 | 0.2 | 0.2 | 0.2 |
| Sodium Chloride[8] | 42.2 | 42.2 | 42.2 | 40 |
| Salicylic acid[9] | 2 | 2 | 2 | 2 |
| Piroctone Olamine[10] | 0.5 | 0.5 | 0.5 | 0.5 |
| Jaguar Excel[11] | | 0.5 | | |
| PVP copolymer[12] (Vinylpyrrolidone/ Dimethylaminoethyl methacrylate) | | | 0.5 | |
| Polyquaternium-10[13] | | | | 0.3 |
| Sodium Benzoate[14] | 0.16 | 0.16 | 0.16 | 0.16 |
| % oil transferred on hair versus Scrub Control at dose of 0.10 g of composition for 1.0 g of hair (Lower is Better) using sebumeter | 60 | 54 | 53 | 54 |
| Rating Hair Oily look vs. Scrub Control at dose of 0.10 g of composition for 1.0 g of hair. 5 for very oily and 1 for not oily | 4 | 3 | 3 | 3 |

[1]Zhishang Huizhou Petrochemicals
[2]Jordapon Ci-Prill, BASF
[3]Miranol Ultra L-32, Solvay
[4]Dehyton KE UP, BASF
[5]Hallstar Italia
[6]L-Menthol Flakes, BASF
[7]Olin Chemicals, Rochester
[8]Merck KGan
[9]Novacyl
[10]Octopirox, Clariant
[11]Solvay
[12]Copolymer 845-O (PVP copolymer), Ashland
[13]UCARE JR30M Extreme Polymer from Dow Inc.
[14]Emerald Kalama Chemical Results: Above table represents scrub compositions that are used for treating hair switches. As shown in the table, hair treated with these compositions has different amount of oil transferred from scalp mimic to hair switch. Hair treated with composition of F, G and H containing hydrophilic polymers makes has less oil transferred vs. control E and are rated low on oiliness look.

Conditioner Treatment Composition Having a Gel Matrix

The conditioner composition may comprise a gel matrix comprising (1) one or more high melting point fatty compounds, (2) a cationic surfactant system, and (3) an aqueous carrier. Cationic surfactant definition captured above.

High Melting Point Fatty Compound

The high melting point fatty compound can be included in the composition at a level of from about 0.5%, or from about 1.0%, or form about 1.5%, or from about 2%, or from about 4%, and to about 15%, and/or from about 10% by weight of the composition. The high melting point fatty compound useful herein have a melting point of 25° C. or higher, or 40° C. or higher, or 45° C. or higher, or 50° C. or higher. The high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

Aqueous Carrier

The conditioner gel matrix of the leave-on treatment composition may include an aqueous carrier which may be water or a mixture of water and water-miscible solvents.

Optional Ingredients in Rinse-Off Shampoo and Conditioner Formulations

Rheology Modifier

The leave-on hair care composition may comprise a rheology modifier to increase the substantivity and stability of the composition. Any suitable rheology modifier can be used. The leave-on hair care composition may comprise 0.05% to 10% (e.g., 0.1%-10%, 0.5% to 2%, 0.7% to 2% or even 1% to 1.5%) of a rheology modifier. Some non-limiting examples of rheology modifiers are listed below.

The rheology modifier may be selected from homopolymers based on acrylic acid, methacrylic acid and the like (e.g., polyacrylate, polymethacrylate, polyethylacrylate, and polyacrylamide); alkali swellable and hydrophobically-modified alkali swellable acrylic copolymers or methacrylate copolymers (e.g., acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylatesisteareth-20 methacrylate crosspolymer, acrylates/vinylneodecanoate crosspolymer, and acrylates/C10-C30 alkyl acrylate crosspolymer); crosslinked acrylic polymers (e.g., carbomers); alginic acid-based materials (e.g., sodium alginate and alginic acid propylene glycol esters); associative polymeric thickeners (e.g., hydrophobically modified cellulose derivatives, hydrophobically modified alkoxylated urethane polymers (e.g., PEG-150/decyl alcohol/SMDI copolymer, PEG-150/stearyl alcohol/SMDI copolymer and polyurethane-39); hydrophobically modified, alkali swellable emulsions (e.g., hydrophobically modified polyacrylates, hydrophobically modified polyacrylic acids, and hydrophobically modified polyacrylamides); hydrophobically modified polyethers (e.g., with a hydrophobe selected from cetyl, stearyl, or oleayl and a hydrophilic portion of repeating ethylene oxide groups (e.g., 10-300 repeating groups, 30-200 repeating groups or even 40-150 repeating groups (e.g., PEG-120-methylglucose dioleate, PEG-(40 or 60) sorbitan tetraoleate, PEG-150 pentaerythrityl tetrastearate, PEG-55 propylene glycol oleate, PEG-150 distearate)); cellulose and its derivatives (e.g., microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses); guar and its derivatives (e.g., hydroxypropyl guar and guar hydroxypropyl trimonium chloride), polyalkyl oxides (e.g., polyethylene oxide, polypropylene oxide, POE-PPO copolymers); polyvinylpyrrolidone, crosslinked polyvinylpyrrolidone, polyvinyalcohol; polyethyleneimine; silicas (e.g., fumed silica, precipitated silica, and surface treated silica); water-swellable clays (e.g., laponite, bentolite, montmorilonite, smectite, and hectonite); gums (e.g., xanthan gum, guar gum, hydroxypropyl guar gum, Arabia gum, tragacanth, galactan, carob gum, karaya gum, and locust bean gum); dibenzylidene sorbitol; carrageenan; pectin; agar; quince seed (Cydonia oblonga Mill); starch (e.g., from rice, corn, potato and wheat); starch-derivatives (e.g. carboxymethyl starch, methylhydroxypropyl starch); algae extracts; dextran; succinoglucan; and pulleran, Further non-limiting examples of rheology modifiers include acrylamide/ammonium acrylate copolymer (and) polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel M C S, Klucel H C S, Klucel G C S, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol Ulterez 30, Carbopol 1342, Sepigel™ 305, Simulgel™600, Sepimax Zen, and combinations thereof.

Some particularly suitable examples of rheology modifiers include derivatives of hydrogenated castor oil (e.g., hydroxystearin compounds) such as 12-hydroxystearic acid (cosmetic grade), available from Kawaken and CasChem, and trihydroxystearin available from Rheox or Elementis Specialies under the Thixcin® brand, Flowtone R available from ECC America, and Rheocin available from United Catalysts.

Carrier

The compositions herein may be leave-on hair care compositions which may further include at least about 20 weight percent of an aqueous carrier. The aqueous carrier is prepared from dermatologically acceptable materials (e.g., demineralized or distilled water). The carrier may be water, organic solvents (miscible or non-miscible with water), silicone solvents or a mixture thereof. In some instances, the carrier may be water with minimal or no significant concentrations of organic solvent, except as otherwise incidentally incorporated into the composition as minor ingredients of other components. The carrier may include volatile solvents that have boiling points below or equal to 250° C.

Some non-limiting examples of carriers include water and solutions or mixtures of water with lower alkyl alcohols and/or polyhydric alcohols. Examples of lower alkyl alcohols are monohydric alcohols having 1 to 6 carbons such as ethanol, methanol, propanol, isopropanol, butanol, pentanol, and hexanol. Examples of polyhydric alcohols are glycols, such as dipropylene glycol, propylene glycol, butylene glycol, 1,4-butanediol, 3-allyloxy-1,2-propanediol, 1,2-hexanediol, 1,6-hexanediol, 1,3-butanediol, 1,3-propanediol, 2,2'-thiodiethanol, glycerin and other diols. Other non-limiting examples of organic solvents include polyglycols such as polypropylene glycol, polyethylene glycol, mixture of butylene glycol, polypropylene glycol, polyethylene glycol and ethers, such as dipropylene glycol n-butyl ether, sugars, and sugar derivatives.

Silicones

The conditioning agent may be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. Nos. 34,584, U.S. Pat. Nos. 5,104,646, and 5,106,609, which descriptions are incorporated herein by reference. The silicone conditioning agents can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering,* vol. 15, 2d ed., pp 204-308, John Wiley & Sons, Inc. (1989), incorporated herein by reference.

Silicone emulsions that may be suitable for use herein include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones,* John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones that may be suitable for use herein include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Anti-Dandruff Actives

The compositions herein may contain anti-dandruff agents. When present in these compositions, the anti-dandruff agent is typically included in an amount of about 0.01 wt. % to about 5 wt. %, based on the total weight of the hair care composition. In these compositions, the anti-dandruff particulate should be physically and chemically compatible with other ingredients of the composition, and should not otherwise unduly impair product stability, aesthetics, or performance.

Anti-dandruff agents suitable for use in hair care compositions include pyridinethione salts, hydroxy pyridones, such as piroctone olamine (octopirox), ciclopirox, rilopirox, and MEA-Hydroxyoctyloxypyridinone, azoles (e.g., ketoconazole, econazole, climbazole and elubiol), selenium sulfide, particulate sulfur, salicylic acid, and mixtures thereof. A typical anti-dandruff agent is as piroctone olamine (octopirox) or pyridinethione salt. Hair care compositions can also include a zinc-containing layered material. An example of a zinc-containing layered material can include zinc carbonate materials. Of these, zinc carbonate and pyridinethione salts (particularly zinc pyridinethione or "ZPT") are common in the composition, and often present together.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Hair Health Actives

A scalp health active may be included in the compositions herein to provide scalp benefits. This group of materials is varied and provides a wide range of benefits including anti-dandruff, anti-fungal, anti-microbial, moisturization, barrier improvement, and anti-oxidant, anti-itch, and sensates. Such skin health actives and scalp care actives include but are not limited to: zinc pyrithione, climbazole, octopirox, selenium sulfide, vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe.

Optional Ingredients

The compositions herein suitable optional ingredients as desired. For example, the composition can optionally include other active or inactive ingredients.

The compositions may include other common hair ingredients such as other anti-dandruff actives, minoxidil, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The hair care compositions herein may be in the form of solutions, dispersion, emulsions, powders, talcs, encapsulated, spheres, spongers, solid dosage forms, foams, and other delivery mechanisms. The composition of the present invention may be rinse off shampoos and conditioners, hair tonics, leave-on hair products such as conditioners, treatment, and styling products, and any other form that may be applied to the hair.

TABLE 1

Rinse off Treatment Formulations

| Formula | Control I (wt/wt) % | Control J (wt/wt) % | Ex. K (wt/wt) % | Ex. L (wt/wt) % | Ex. M (wt/wt) % | Ex. N (wt/wt) % |
|---|---|---|---|---|---|---|
| Stearamidopropyldimethyl amine (SAPDMA)[1] | 1.95 | 0 | 1.95 | 1.95 | 0 | 0 |
| BTMS/IPA[2] | 0 | 1.95 | 0 | 0 | 1.95 | 1.95 |
| Cetyl Alcohol[3] | 1.77 | 1.7 | 1.77 | 1.77 | 1.7 | 1.7 |
| Stearyl Alcohol[4] | 3.05 | 4.3 | 3.05 | 3.05 | 4.3 | 4.3 |
| Disodium EDTA[5y] | 0.13 | 0.1 | 0.13 | 0.13 | 0.1 | 0.1 |
| Benzyl Alcohol[6] | 0.4 | 0.4 | 0.4 | 0.4 | 0.4 | 0.4 |
| Perfume | 1 | 0.7 | 1 | 1 | 0.7 | 0.7 |
| PVP copolymer7(Vinylpyrrolidone/ Dimethylaminoethyl methacrylate) | 0 | 0 | 0 | 0.3 | 0.3 | 0 |
| Sodium Hyaluronate[8] | 0 | 0 | 0.3 | 0 | 0 | 0.3 |
| DI Water | Q.S. | Q.S. | Q.S. | Q.S. | Q.S. | Q.S. |
| % oil transferred on hair versus Rinse of treatment respective control at dose of 0.10 g of composition for 1.0 g of hair (Lower is Better) using sebumeter | 66 | 72 | 57 | 56 | 68 | 67 |

TABLE 1-continued

| Rinse off Treatment Formulations | | | | | | |
|---|---|---|---|---|---|---|
| Formula | Control I (wt/wt) % | Control J (wt/wt) % | Ex. K (wt/wt) % | Ex. L (wt/wt) % | Ex. M (wt/wt) % | Ex. N (wt/wt) % |
| Rating Hair Oily look vs. Rinse of treatment respective Control at dose of 0.10 g of composition for 1.0 g of hair. 5 for very oily and 1 for not oily | 3 | 4 | 2 | 2 | 3 | 3 |

[1]Genamin SPA, Clariant
[2]Supplied by Feixiang Chemicals (Zhangjingang) Co., Ltd.
[3]Supplied by P&G Chemicals
[4]Supplied by P&G Chemicals
[5]Trilon BD Powder supplied by BASF SE (Ludwigshafen, DE)
[6]Supplied by Ineos Maastricht BV (Maastricht NL)
[7]Copolymer 845-O (PVP copolymer), Ashland
[8]P&G Shiga Plant Results: Table 1 represents rinse-off conditioner compositions that are used for treating hair switches. As shown in the table, hair treated with these compositions has different amount of oil transferred from scalp mimic to hair switch. Hair treated with composition of Control I makes has less oil transferred vs. control J, as SAPDMA makes hair more polar than BTMS. In addition Example K and L containing hydrophilic PVP copolymer and sodium hyaluronate in addition to SAPDMA further reduce % amount of oil transferred from scalp mimic to hair switch vs. control I without these hydrophilic polymers. Similarily, Example M and N containing hydrophilic PVP copolymer and sodium hyaluronate in addition to BTMS further reduce % amount of oil transferred from scalp mimic to hair switch vs. control J without these hydrophilic polymers.

Regimen

Benefits for reducing oil transfer from scalp to hair may be achieved by a hair treatment regimen comprising a shampoo composition followed by treating the hair with rinse-off or leave-on composition or a scrub. In the present invention, the regimen may comprise both rinse-off and leave-on treatments with rinse-off and leave-on conditioner compositions.

TABLE 2

| Regimen Examples at each step may contain 1 or more of hydrophilic polymers and cationic surfactant. | | | | | | |
|---|---|---|---|---|---|---|
| Regimen Steps | Regimen Example 12 | Regimen Example 13 | Regimen Example 14 | Regimen Example 15 | Regimen Example 16 | Regimen Example 17 |
| Step 1 | Shampoo (Example D) | Scrub* (Example H) | Shampoo (Example D) | Shampoo (Example D) | Shampoo (Example D) | Shampoo (Example D) |
| Step 2 | Scrub* (Example H) | Shampoo (Example D) | Scrub* (Example H) | Conditioner (Example L) | Scrub* (Example H) | Leave-on (Example 11) |
| Step 3 | Conditioner (Example L) | Conditioner (Example L) | Leave-on (Example 11) | Leave-on (Example 11) | | |
| Step 4 | Leave-on (Example 11) | Leave-on (Example 11) | | | | |

*Scrub Treatment Time (T) and Dosage (D) may vary from regimen to regimen

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art. To the extent that any meaning or definition of a term in this document conflicts with any meaning or definition of the same term in a document incorporated by reference, the meaning or definition assigned to that term in this document shall govern.

While particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition, comprising:

about 0.05% to 5% of a hydrophilic polymer selected from the group consisting of polyvinylalcohols, polyacrylates ethers, polyvinyl pyrrolidones, polyvinyl pyrrolidone copolymers, vinyl cyanides, vinyl phosphates, vinyl phosphonates, vinyl sulfates, vinyl sulfonates, polyamines, cellulose, collagen, polyethylene glycols, polycarboxylate co-polymers of maleic/olefin and mixtures thereof, wherein the hair care composition further comprises a surfactant, a conditioning agent and about 0.01% to 5% of an anti-dandruff active selected from the group consisting of pyridinethione salts, hydroxy pyridones, azoles, selenium sulfide, particulate sulfur, salicylic acid, and mixtures thereof, wherein the hair care composition provides a water contact angle of less than 85 to hair, when measured with a mobile surface analyzer.

2. The hair care composition according to claim 1, wherein there is a decrease in total lipid value on hair compared to a control using Fourier-Transform Infra-red spectroscopy method (FTIR).

3. The hair care composition according to claim 2 wherein the total lipid value on hair is less than 0.15 measured using FTIR.

4. The hair care composition according to claim 2 wherein the total lipid value on hair is less than 0.11 measured using FTIR.

5. The hair care composition according to claim 2, wherein the total lipid value on hair is less than 0.09 measured using FTIR.

6. The hair care composition according to claim 1, wherein the hair care composition provides a water contact angle of less than 80 to hair.

7. The hair care composition according to claim 1, wherein the hair care composition provides a water contact angle of less than 75 to hair.

8. The hair care composition according to claim 1, wherein the hydrophilic polymer is about 0.05% to 3%.

9. The hair care composition according to claim 1, wherein the hydrophilic polymer is about 0.1% to 2%.

10. The hair care composition according to claim 1, wherein the hydrophilic polymer is about 0.2% to 1%.

11. The hair care composition according to claim 1, wherein the hydrophilic polymer is selected from the group consisting of vinylpyrrolidone/dimethylaminoethyl methacrylate acrylic copolymer, mono-long alkyl amidoamine salt, polyquaternium-10 and mixtures thereof.

12. The hair care composition according to claim 1, further comprising an anionic, amphoteric, nonionic or zwitterionic surfactant or mixtures thereof.

13. The hair care composition according to claim 1, further comprising a cationic polymer.

14. The hair care composition according to claim 1, wherein the hydroxyl pyridone is piroctone olamine.

15. The hair care composition according to claim 1, wherein the conditioning agent is a silicone.

16. The hair care composition according to claim 1, further comprising about 0.5% to about 7% of a perfume.

* * * * *